(12) United States Patent
Ogasawara

(10) Patent No.: US 8,477,182 B2
(45) Date of Patent: Jul. 2, 2013

(54) ENDOSCOPE APPARATUS AND CONTROL METHOD OF ENDOSCOPE APPARATUS

(75) Inventor: Kotaro Ogasawara, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/594,031

(22) Filed: Aug. 24, 2012

(65) Prior Publication Data
US 2013/0050454 A1   Feb. 28, 2013

Related U.S. Application Data

(63) Continuation of application No. PCT/JP2011/065982, filed on Jul. 13, 2011.

(30) Foreign Application Priority Data

Jul. 26, 2010 (JP) ................... 2010-167203

(51) Int. Cl.
*A62B 1/04* (2006.01)
(52) U.S. Cl.
USPC .......................................................... 348/65
(58) Field of Classification Search
None
See application file for complete search history.

(56) References Cited

U.S. PATENT DOCUMENTS

| 5,209,220 | A | * | 5/1993 | Hiyama et al. | 600/109 |
| 5,272,538 | A | | 12/1993 | Homma et al. | |
| 7,029,437 | B2 | * | 4/2006 | Kobayashi | 600/180 |
| 7,852,513 | B2 | * | 12/2010 | Donomae | 358/2.1 |
| 8,269,862 | B2 | * | 9/2012 | Sasaki | 348/241 |
| 8,284,245 | B2 | * | 10/2012 | Takemura et al. | 348/71 |
| 8,305,427 | B2 | * | 11/2012 | Yamazaki et al. | 348/46 |
| 2002/0004626 | A1 | | 1/2002 | Abe | |
| 2006/0171605 | A1 | * | 8/2006 | Watanabe | 382/274 |

FOREIGN PATENT DOCUMENTS

| JP | 01-120180 | 5/1989 |
| JP | 05-137060 | 6/1993 |
| JP | 09-046581 | 2/1997 |
| JP | 09-262206 | 10/1997 |
| JP | 2001-154232 | 6/2001 |
| JP | 2002-014291 | 1/2002 |
| JP | 2002-300468 | 10/2002 |
| JP | 2003-046858 | 2/2003 |
| JP | 2004-267290 | 9/2004 |
| JP | 2005-021423 | 1/2005 |
| JP | 2006-034796 | 2/2006 |

OTHER PUBLICATIONS

International Search Report dated Aug. 30, 2011 issued in PCT/JP2011/065982.

* cited by examiner

*Primary Examiner* — Nhon Diep
(74) *Attorney, Agent, or Firm* — Scully, Scott, Murphy & Presser, P.C.

(57) ABSTRACT

An endoscope apparatus includes: a region dividing portion that divides an image; a brightness mean calculation portion that has a peripheral brightness mean calculation portion that calculates a peripheral brightness mean value, and a center brightness mean calculation portion that calculates a center brightness mean; a first weighting factor calculation portion that calculates a first weighting factor α; a first photometric value calculation portion that calculates a first photometric value based on a sum total of a value obtained by multiplying a center brightness mean by the first weighting factor α and a value obtained by multiplying the peripheral brightness mean by (1−α); and a brightness adjustment control portion that generates a brightness adjustment control signal for adjusting the brightness of the image based on the first photometric value.

8 Claims, 8 Drawing Sheets

CENTER BRIGHTNESS MEAN VALUE/
PERIPHERAL BRIGHTNESS MEAN VALUE (-)

ENDOSCOPE APPARATUS AND CONTROL METHOD OF ENDOSCOPE APPARATUS

CROSS REFERENCE TO RELATED APPLICATION

This application is a continuation application of PCT/JP2011/065982 filed on Jul. 13, 2011 and claims benefit of Japanese Application No. 2010-167203 filed in Japan on Jul. 26, 2010, the entire contents of which are incorporated herein by this reference.

BACKGROUND OF INVENTION

1. Field of the Invention

The present invention relates to an endoscope apparatus that has a function that adjusts the brightness of an endoscope image, and a control method for the endoscope apparatus.

2. Description of the Related Art

In order to photograph a dark inside of a body cavity and obtain an endoscope image with proper brightness, an endoscope apparatus illuminates the inside of the body cavity with an illuminating light that has an automatic light adjustment function and performs brightness adjustment processing with respect to an image that is picked up. As the automatic light adjustment function, a diaphragm of a light source apparatus is controlled to adjust an amount of light in accordance with the brightness of the endoscope image that is calculated by a photometry portion that calculates the brightness of an object.

In Japanese Patent Application Laid-Open Publication No. 2001-154232 and Japanese Patent Application Laid-Open Publication No. 2004-267290, the applicants disclose an electronic endoscope apparatus and the like that adopts a mean photometric method that is based on a mean value of brightness with respect to a part that corresponds to a periphery part in an image pickup range and adopts a peak photometric method that is based on a peak value of brightness for a center part in the image pickup range to thereby enable observation with the optimal brightness. Compared to a photometric method that is based on a mean value of the brightness of an entire screen, according to this photometric method more appropriate brightness control can be performed when observing a gastric angle part or the like that contains a region of interest of a user at a center region.

When observing a lumen-shaped object such as the large intestine or the esophagus, there are many cases in which there is a lumen on a deep side in a center region of the image and there is a luminal wall at a peripheral region of the image. Because the lumen on the deep side is far from the distal end portion of the endoscope in which an illumination portion is disposed, the lumen on the deep side is dark. In contrast, the luminal wall that has the region of interest of the user is near to the distal end portion of the endoscope, and is therefore bright. When using an endoscope apparatus that measures brightness and adjusts the light amount by taking the entire region of an endoscope image as an object, a luminal wall at a peripheral region of the endoscope image becomes too bright. Consequently, it has been necessary for the user to perform an operation to bend the distal end portion so that the region of interest becomes the center region of the endoscope image.

SUMMARY OF THE INVENTION

An endoscope apparatus according to an embodiment of the present invention includes: a region dividing portion that divides an endoscope image into a center region and a peripheral region; a brightness mean value calculation portion that has a peripheral brightness mean value calculation portion that calculates a peripheral brightness mean value that indicates a mean value of a brightness of the peripheral region, and a center brightness mean value calculation portion that calculates a center brightness mean value that indicates a mean value of a brightness of the center region; a first weighting factor calculation portion that calculates a first weighting factor α (where 0<α<1) based on a ratio between the center brightness mean value and the peripheral brightness mean value; a first photometric value calculation portion that calculates a first photometric value based on a sum total of a value obtained by multiplying the center brightness mean value by the first weighting factor α and a value obtained by multiplying the peripheral brightness mean value by (1−α); and a brightness adjustment control portion that generates a brightness adjustment control signal that adjusts a brightness of the endoscope image based on the first photometric value; wherein when the ratio between the peripheral brightness mean value and the brightness mean value is in a predetermined range that is centered around a value of 1, even if the ratio changes, the weighting factor calculation portion calculates the first weighting factor α of a same value.

A control method for an endoscope apparatus according to an embodiment of the present invention includes: a region dividing step in which a region dividing portion divides an endoscope image into a center region and a peripheral region; a peripheral brightness mean value calculation step in which a peripheral brightness mean value calculation portion calculates a peripheral brightness mean value that indicates a mean value of a brightness of the peripheral region; a center brightness mean value calculation step in which a center brightness mean value calculation portion calculates a center brightness mean value that indicates a mean value of a brightness of the center region; a first weighting factor calculation step in which a weighting factor calculation portion calculates a first weighting factor α (where 0<α<1) based on a ratio between the center brightness mean value and the peripheral brightness mean value; a first photometric value calculation step in which a first photometric value calculation portion calculates a first photometric value based on a sum total of a value obtained by multiplying the center brightness mean value by the first weighting factor α and a value obtained by multiplying the peripheral brightness mean value by (1−α); and a brightness adjustment control step in which a brightness adjustment control portion generates a brightness adjustment control signal that adjusts a brightness of the endoscope image based on the first photometric value; wherein, in the weighting factor calculation step, when the ratio between the peripheral brightness mean value and the brightness mean value is in a predetermined range that is centered around a value of 1, even if the ratio changes, the weighting factor calculation portion calculates the first weighting factor α of a same value.

DETAILED DESCRIPTION OF THE PREFERRED EMBODIMENT(S)

<First Embodiment>

Figure 1:
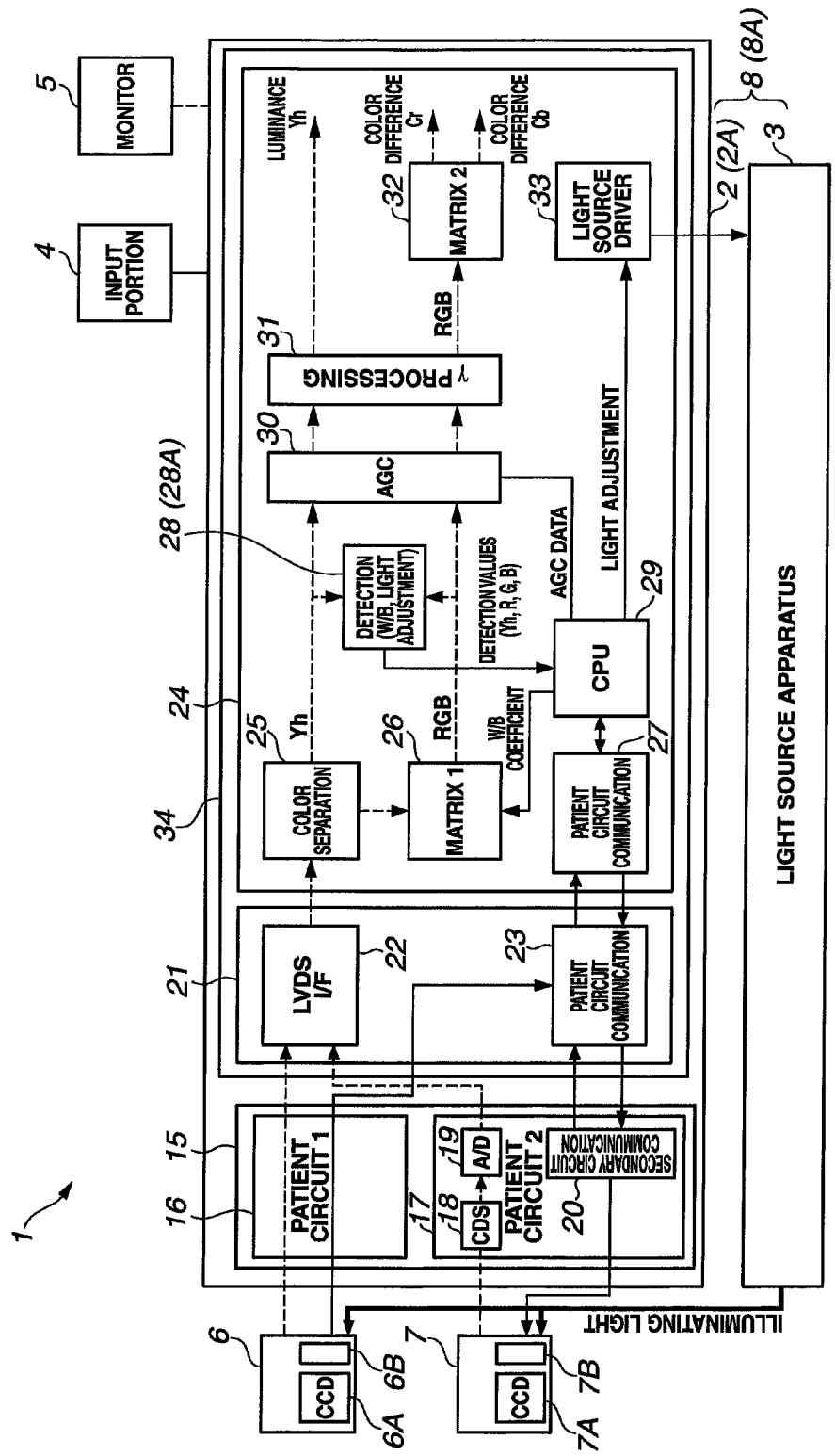
FIG. 1 is a configuration diagram of an endoscope system having an endoscope apparatus according to a first embodiment.

As shown in FIG. 1, an endoscope system 1 includes a processor 2, endoscopes 6 and 7, a light source apparatus 3, an input portion 4, and a monitor 5. In FIG. 1, dashed lines indicate the flow of video signals and solid lines indicate the flow of control signals. The endoscope 6 is a digital endoscope that has a CCD 6A that is image pickup means and an unshown A/D conversion circuit, and that outputs a digital video signal. On the other hand, the endoscope 7 is an analog endoscope that has a CCD 7A that is image pickup means, and that outputs an analog video signal. The CCDs 6A and 7A change the speeds of electronic shutters 6B and 7B and thereby constitute one of a plurality of brightness adjustment portions that adjust the brightness of an endoscope image.

Note that although in the endoscope system 1 the endoscope 6 is connected to the processor 2, the endoscope 6 may also be connected via the light source apparatus 3. Although an endoscope apparatus 8 according to the embodiment has the processor 2 and the light source apparatus 3, a configuration may also be adopted in which the endoscope apparatus 8 has only the processor 2.

In the endoscope apparatus 8, a circuit system (patient circuit) that is inserted into the body of a patient and a circuit portion (secondary circuit) 34 that is connected to peripheral equipment such as a monitor are insulated to ensure safety. A patient circuit 15 of the processor 2 includes a patient circuit 1 (16) and a patient circuit 2 (17). Each of the aforementioned patient circuits are formed on separate wiring boards and are insulated with respect to each other. The patient circuit 1 (16) is connected to the endoscope 6. The patient circuit 2 (17) is connected to the endoscope 7.

The patient circuit 2 (17) includes circuits for sampling an analog video signal inputted from the endoscope 7 and converting the analog video signal to a digital video signal, for example, a CDS (correlated double sampling) portion 18 and an A/D portion 19, and also includes a secondary circuit communication portion 20 that performs communication of control signals with respect to the secondary circuit.

A video signal is transmitted to a signal processing portion 24 through a serial digital I/F such as an LVDS (low voltage differential signaling) I/F (22), for example. The signal processing portion 24 includes a color separation portion 25, a matrix 1 (26), a detection portion 28, an AGC (automatic gain control) portion 30, a γ processing portion 31, a matrix 2 (32), a patient circuit communication portion (27), a light source driver 33, and a CPU 29. The AGC portion 30 adjusts an amplification factor (gain) and thereby constitutes one of the brightness adjustment portions that adjust the brightness of an endoscope image.

The light source apparatus 3 has a light source that generates an illuminating light such as, for example, a xenon lamp, and a diaphragm portion that adjusts a light amount of an illuminating light and the like. The light source apparatus 3 illuminates a subject from a distal end portion through respective light guides of the endoscopes 6 and 7 that are connected thereto. The light source apparatus 3 adjusts an electric current that is fed to the light source, adjusts an aperture ratio of the diaphragm portion, or adjusts an emitted light amount, and thereby constitutes one of the brightness adjustment portions that adjust the brightness of an endoscope image.

The detection portion 28 detects a video signal that constitutes an endoscope image and has a function of a photometry portion that processes information regarding the brightness thereof and the like. The CPU 29 performs control of the entire endoscope apparatus 8, and also has a function of a brightness adjustment control portion that controls a brightness adjustment portion as described later.

The input portion 4 is a keyboard or the like with which a user inputs instructions for operation of the endoscope apparatus 8 and the like. Note that a switch of an operation portion of the endoscope or the like may also be used as an input portion. The monitor 5 is display means that displays an endoscope image 5A. Note that although in the endoscope system 1 the two endoscopes 6 and 7 can be connected at the same time to the endoscope apparatus 8, only either one of the endoscopes can be driven.

Figure 2:
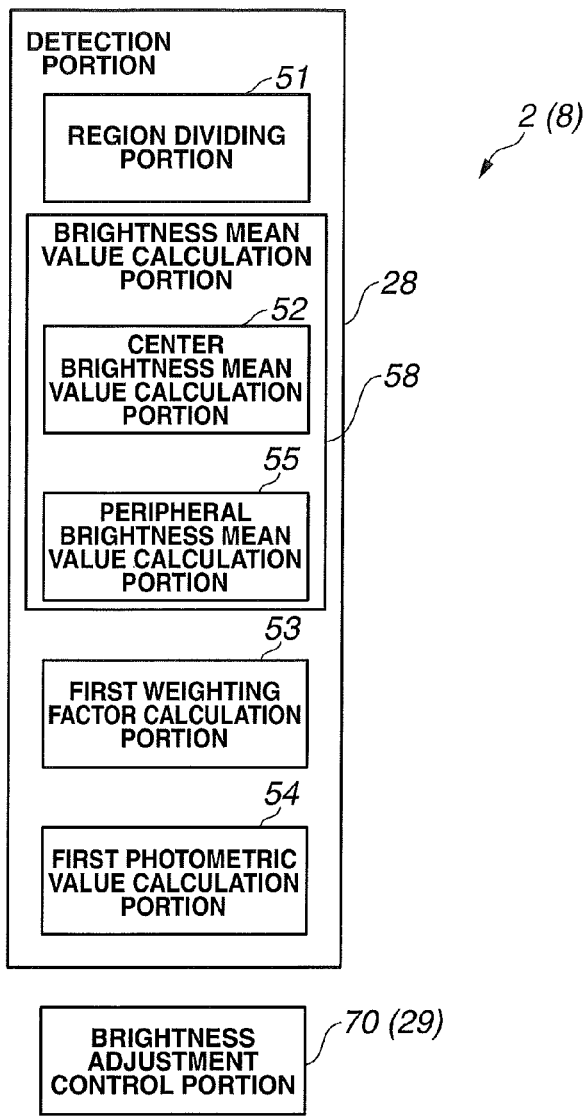
FIG. 2 is a configuration diagram of a photometry portion of the first embodiment.

As shown in FIG. 2, the detection portion 28 of the endoscope apparatus 8 includes: a region dividing portion 51 that is region dividing means; a brightness mean value calculation portion 58 that is brightness mean value calculation means that has a center brightness mean value calculation portion 52 as center brightness mean value calculation means and a peripheral brightness mean value calculation portion 55 as peripheral brightness mean value calculation means; a first weighting factor calculation portion 53 that is first weighting factor calculation means; and a first photometric value calculation portion 54 that is first photometric value calculation means. As described in the foregoing, a brightness adjustment control portion 70 that is brightness adjustment control means is, for example, a part of the functions of the CPU 29.

The region dividing portion 51 divides an endoscope image that the CCD (6A) of the endoscope 6 or the CCD (7A) of the endoscope 7 has captured into n (n is an integer of 3 or more) regions that include a center region and (n−1) peripheral regions. The peripheral brightness mean value calculation portion 55 calculates a peripheral brightness mean value that indicates a mean value of the brightness of the peripheral regions. The center brightness mean value calculation portion 52 calculates a center brightness mean value that indicates a mean value of the brightness of the center region. That is, the brightness mean value calculation portion 58 calculates brightness mean values of the n regions. The first weighting factor calculation portion 53 calculates a first weighting factor α (where 0<α<1) based on a ratio between the center brightness mean value that is the brightness mean value of the center region and the peripheral brightness mean value. The brightness adjustment control portion 70 generates a brightness adjustment control signal for adjusting the brightness of the endoscope image based on a first photometric value.

Note that it is not necessary for the respective functional portions shown in FIG. 2 to be independent components, and the respective functional portions may be realized by operation of software. Further, at least a part of the functional portion of the detection portion 28 may be realized by the CPU 29 or an unshown sub-CPU or the like.

Figure 5:
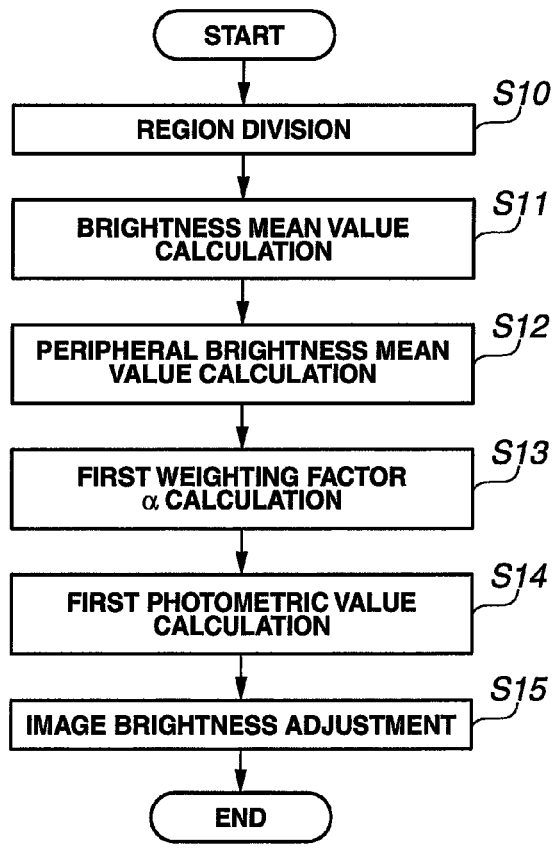
FIG. 5 a flowchart for describing the flow of processing of the photometry portion of the first embodiment.

Hereunder, a brightness adjustment method of the endoscope apparatus 8 is described in accordance with the flowchart shown in FIG. 5.

<Step S10> Region Dividing Step

Figure 3:
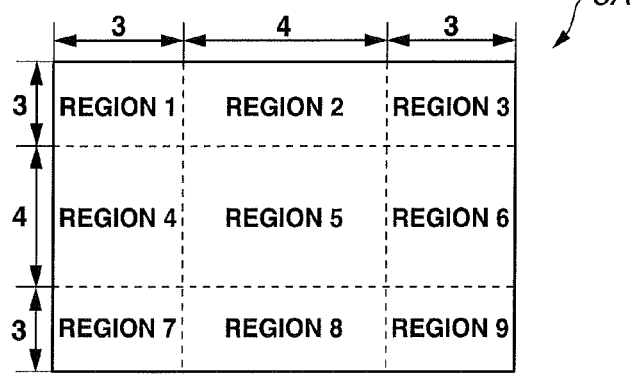
FIG. 3 is an explanatory view for describing a first weighting factor of the photometry portion of the first embodiment.

As shown in FIG. 3, the region dividing portion 51 divides the endoscope image 5A into n (n is an integer of 2 or more; in this case n=9) regions that include one center region (region 5) and 8 peripheral regions (regions 1 to 4 and 6 to 9). Although in FIG. 3 an example is shown in which the method of dividing the endoscope image into n regions is a method that divides the endoscope image with a ratio of 3:4:3 both vertically and horizontally, the method of dividing is not limited thereto. Further, the number of divisions and the shapes of the divided regions are not limited to the example shown in FIG. 3. Note that in the endoscope apparatus 8 of the present embodiment, it is sufficient that division is performed into two regions that include a center region and a peripheral region. That is, it is sufficient that n=2 and that the region dividing portion 51 divides the endoscope image into two regions that include a center region and a peripheral region.

<Step S11> Brightness Mean Value Calculation Step

The brightness mean value calculation portion 58 calculates brightness mean values of the n (n=9) regions. One of the brightness mean values of the n regions is a center brightness mean value that is the brightness mean value of the center region (region 5).

<Step S12> Peripheral Brightness Mean Value Calculation Step

The peripheral brightness mean value calculation portion 55 calculates a peripheral brightness mean value that is a mean value of the brightness mean values of the eight peripheral regions (regions 1 to 4 and 6 to 9).

Note that, to reduce the circuit scale and the software load, it is preferable that mean value calculation processing that uses luminance values of all pixels of the endoscope image 5A is performed using luminance values of so-called "thinned-out" pixels that are obtained by skipping pixels at regular intervals. Further, pixels that are brighter than a predetermined threshold value and pixels that are darker than a predetermined threshold value need not be used in the processing. The same applies with respect to the processing that is described below.

<Step S13> First Weighting Factor Calculation Step

The first weighting factor calculation portion 53 calculates the first weighting factor $\alpha$ (where $0<\alpha<1$) based on the ratio between the center brightness mean value and the peripheral brightness mean value.

Figure 4:
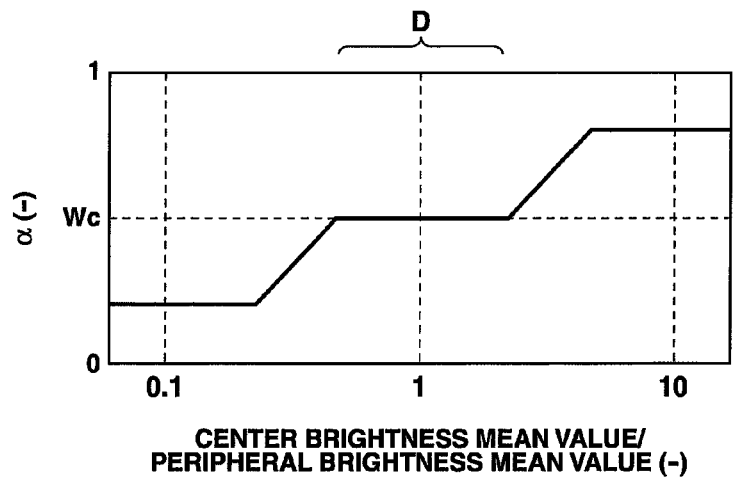
FIG. 4 is an explanatory view that shows a region of an endoscope image that is divided by the photometry portion of the first embodiment.

In this case, the first weighting factor calculation portion 53 calculates the first weighting factor $\alpha$ using, for example, a calculation function. In a calculation function graph shown in FIG. 4, the horizontal axis represents a ratio between the center brightness mean value and the peripheral brightness mean value and the vertical axis represents the first weighting factor $\alpha$. The calculation function is not a function that monotonously increases, but rather is a function such that, in a predetermined range D that is centered around a point at which the ratio between the peripheral brightness mean value and the center brightness mean value is 1, even if the ratio changes, the first weighting factor $\alpha$ is the same value, for example, Wc. Further, when the ratio between the peripheral center brightness mean value and the center brightness mean value is less than or equal to a predetermined value and greater than or equal to a predetermined value, the first weighting factor $\alpha$ does not change.

That is, the first weighting factor $\alpha$ has an upper limit value, a lower limit value, and a median value, and a dead zone is provided at the median value Wc. Therefore, the brightness of the endoscope image 5A can be stably controlled.

Note that the first weighting factor calculation portion 53 is not limited to the use of a function (numerical formula) for calculating the first weighting factor $\alpha$, and may also use a table that includes numeric data or the like.

<Step S14> First Photometric Value Calculation Step

The first photometric value calculation portion 54 calculates a first photometric value based on a sum total of a value obtained by multiplying the center brightness mean value by the first weighting factor $\alpha$ and a value obtained by multiplying the peripheral brightness mean value by $(1-\alpha)$.

<Step S15> Brightness Adjustment Step

Based on the first photometric value that is calculated by the first photometric value calculation portion 54, the brightness adjustment control portion 70 generates a brightness adjustment control signal and sends the brightness adjustment control signal to the brightness adjustment portion to thereby control the brightness adjustment portion. That is, the brightness adjustment portion adjusts the brightness of the endoscope image 5A based on the brightness adjustment control signal. Here, the term "brightness adjustment portion" refers to at least any one of the AGC portion 30, the diaphragm portion of the light source apparatus 3, and the electronic shutters 6B and 7B of the endoscopes 6 and 7.

Figure 6:
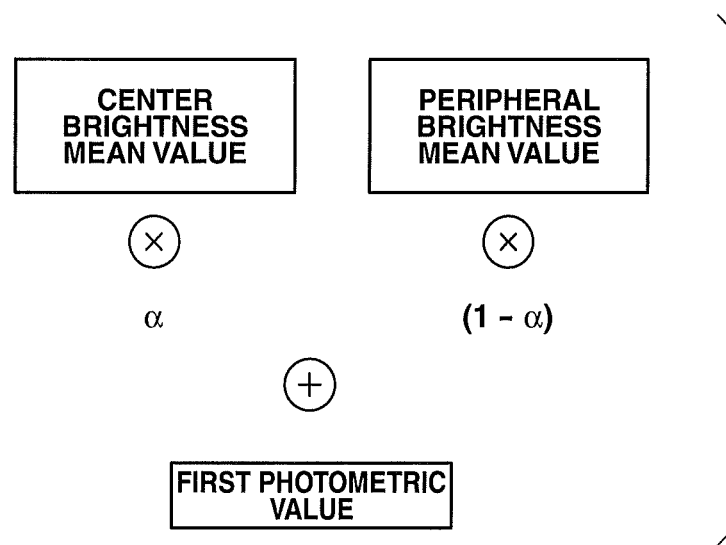
FIG. 6 is an explanatory view for describing processing of the photometry portion of the first embodiment.

As described above, in the endoscope apparatus 8 of the present embodiment, the brightness of the endoscope image 5A is controlled based on the first photometric value that is calculated by processing shown in FIG. 6. Therefore, photometry is performed in such a manner as to emphasize a region with a high luminance (that is, a region the observer is focusing attention on) among the center region and peripheral regions of the endoscope image 5A, and brightness adjustment of the endoscope image 5A is performed based on the photometry result. Consequently, the endoscope apparatus 8 that has good operability can be provided. Likewise, according to the control method for the endoscope apparatus of the present embodiment, it is possible to provide a control method for an endoscope apparatus that has good operability.

<Second Embodiment>

An endoscope apparatus 8A according to the second embodiment of the present invention is similar to the endoscope apparatus 8 of the first embodiment, and hence the same components are denoted by the same reference symbols and a description of such components is omitted hereunder.

Figure 7:
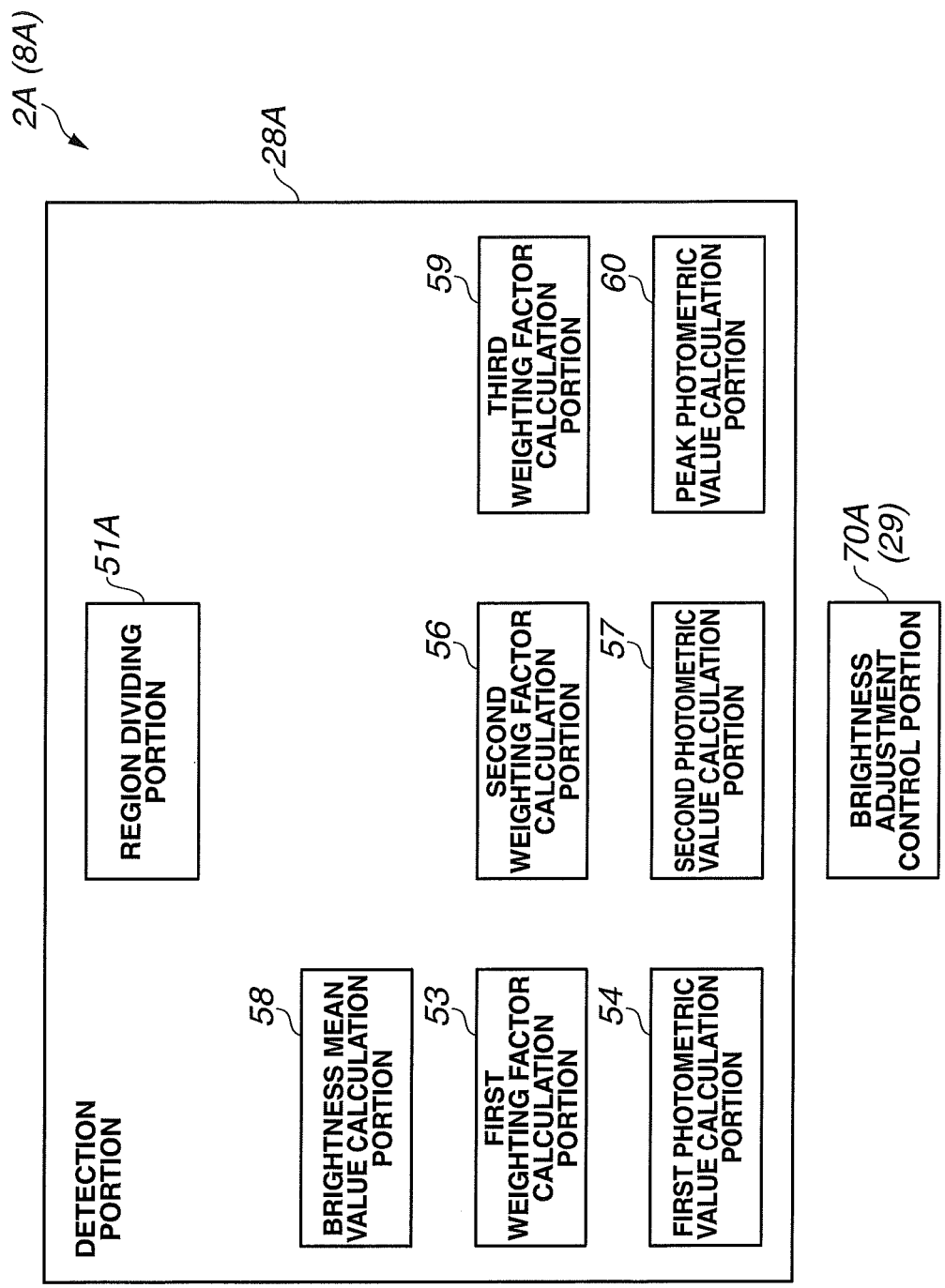
FIG. 7 is a configuration diagram of a photometry portion of a second embodiment.

As shown in FIG. 7, in addition to, or in place of, the components of the detection portion 28, a detection portion 28A of the endoscope apparatus 8A further includes a second weighting factor calculation portion 56 that is second weighting factor calculation means, a second photometric value calculation portion 57 that is second photometric value calculation means, a third weighting factor calculation portion 59 that is third weighting factor calculation means, a peak photometric value calculation portion 60 that is peak photometric value calculation means, and a brightness adjustment control portion 70A.

The second weighting factor calculation portion 56 calculates a second weighting factor $\beta$ (where $0<\beta<1$). The second photometric value calculation portion 57 calculates a second photometric value based on a sum total of a value obtained by multiplying the first photometric value by the second weighting factor $\beta$ and a value obtained by multiplying the peak photometric value by $(1-\beta)$.

The third weighting factor calculation portion 59 calculates third weighting factors $\gamma1$ to $\gamma9$. The peak photometric value calculation portion 60 calculates a peak photometric value by sorting the regions 1 to 9 into which the endoscope image has been divided in the order of brightness and multiplying the respective brightness values by the weighting factors γ1 to 9 and adding the results. That is, the peak photometric value is a value that does not depend on the brightest region in the endoscope image 5A or on a position (region) calculated by means of pixel values.

Note that, the second weighting factor β that the second weighting factor calculation portion 56 calculates and the third weighting factors γ1 to γn that the third weighting factor calculation portion 59 calculates may also be fixed values that are previously set, and not values that change according to the conditions as in the case of the first weighting factor α. That is, the second weighting factor calculation portion 56 and the third weighting factor calculation portion 59 may be storage portions in which predetermined weighting factors are stored.

The second photometric value calculation portion 57 calculates the second photometric value based on a sum total of a value obtained by multiplying the first photometric value by the second weighting factor β and a value obtained by multiplying the peak photometric value by (1−β). The brightness adjustment control portion 70A generates a brightness adjustment control signal in the same manner as the brightness adjustment control portion 70.

It is not necessary for the above described components to be independent components, and the respective components may be realized by the operation of software. Further, the operations thereof may be performed by the CPU 29 or the like.

Figure 8:
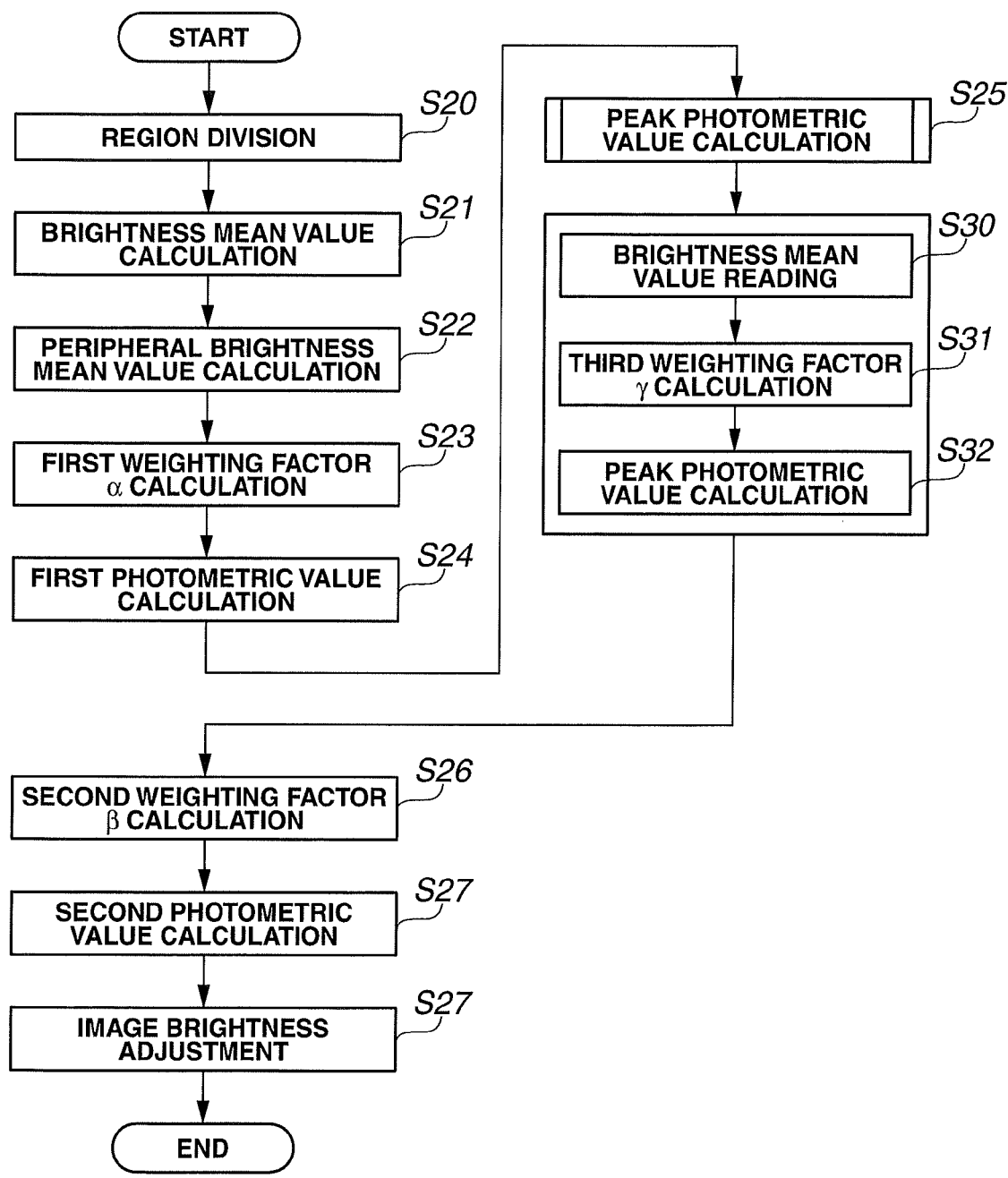
FIG. 8 is a flowchart for describing the flow of processing of the photometry portion of the second embodiment.

Hereunder, a brightness adjustment method of the endoscope apparatus 8A is described in accordance with the flowchart shown in FIG. 8.

<Steps S20 to S24> Region Dividing Step to First Photometric Value Calculation Step These steps are the same as steps S10 to S14 of the endoscope apparatus 8 of the first embodiment, and hence a description thereof is omitted here. However, in the region dividing step S20, a region dividing portion 51A divides the endoscope image into n (n≧3) regions.

<Step S25> Peak Photometric Value Calculation Step

A peak photometric value is calculated using a peak photometric value calculation subroutine that is described later.

<Step S26> Second weighting factor calculation step

The second weighting factor calculation portion 56 calculates the second weighting factor β by calling up a predetermined third weighting factor β that had been stored. Here, 0<β<1.

<Step S27> Second Photometric Value Calculation Step

The peak photometric value calculation portion 60 calculates a second photometric value based on a sum total of a value obtained by multiplying the first photometric value by the second weighting factor β and a value obtained by multiplying the peak photometric value by (1−β).

<Step S28> Brightness Adjustment Step

The brightness adjustment control portion 70A generates a brightness adjustment control signal for adjusting the brightness of the endoscope image 5A based on the second photometric value.

Next, the peak photometric value calculation subroutine shown in FIG. 8 will be described.

<Step S30> Brightness Mean Value Calculation Step

The n brightness mean values calculated in step S21 are called up from an unshown storage portion or the like. Naturally, a configuration may also be adopted in which the n brightness mean values are calculated once more.

Note that although n=9 in the division example shown in FIG. 3, it is sufficient that n is equal to or greater than 3.

Further, the higher the number of divisions is, the peakier the photometric value that can be obtained, and light amount adjustment can be performed in a manner that is preferable as a peak photometry mode.

<Step S31> Third Weighting Factor Calculation Step

The third weighting factor calculation portion 59 calculates n third weighting factors γ1 to γn that correspond to the order of the sizes of the n brightness mean values. Here, 0<γ<1, and Σγ=(γ1+γ2+ . . . +γn)=1. In the example shown in FIG. 10, the third weighting factor γ1 corresponds to the brightest brightness mean value, and the second weighting factor γ9 corresponds to the darkest brightness mean value. For example, the third weighting factor γ is set so that the brighter that the relevant region is, the higher that the value of the third weighting factor becomes.

<Step S32> Peak Photometric Value Calculation Step

The peak photometric value calculation portion 60 calculates a peak photometric value based on a sum total of n multiplication values that are obtained by multiplying the respective n brightness mean values by the respective third weighting factors γ1 to γn that correspond to the order of the sizes of the n brightness mean values.

Figure 10:
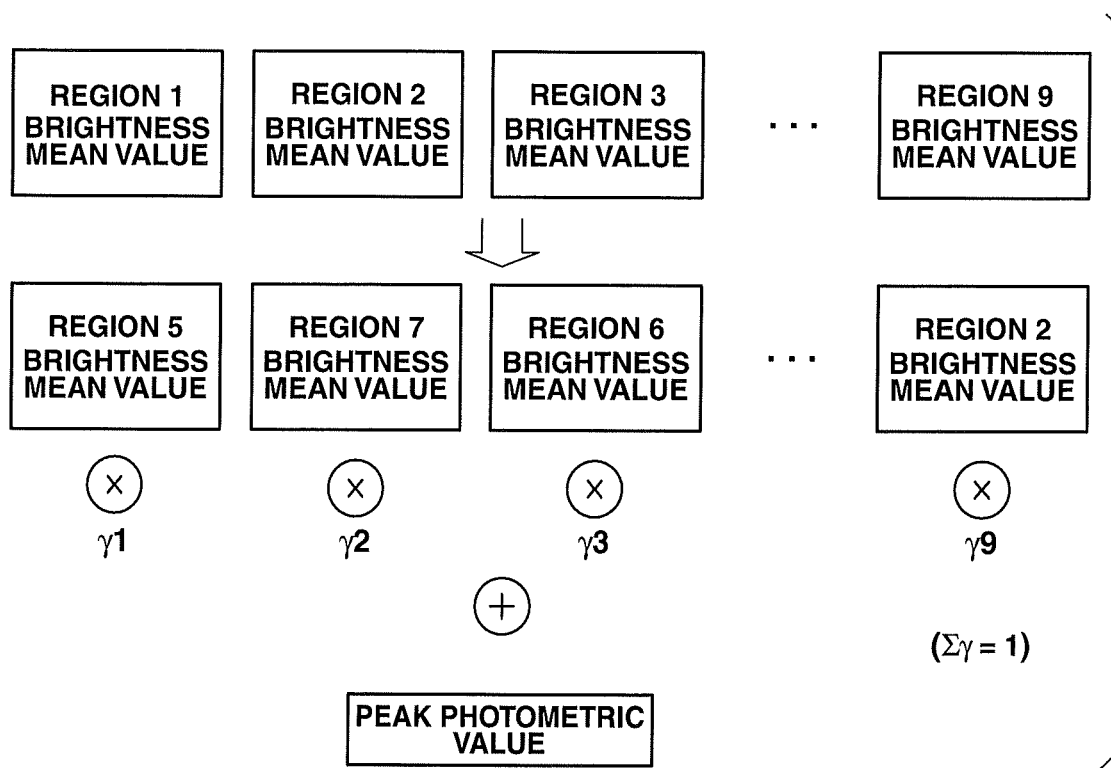
FIG. 10 is an explanatory view for describing peak photometric value calculation processing of the second embodiment.

For example, in the example shown in FIG. 10, region 5 has the largest brightness mean value, and therefore the brightness mean value of region 5 is multiplied by γ1. Likewise, region 7 has the second largest brightness mean value, and therefore the brightness mean value of region 7 is multiplied by γ2. Further, region 2 has the smallest brightness mean value, and therefore the brightness mean value of region 2 is multiplied by γ9. The peak photometric value is calculated by adding up the nine values that are obtained by multiplication.

Figure 9:
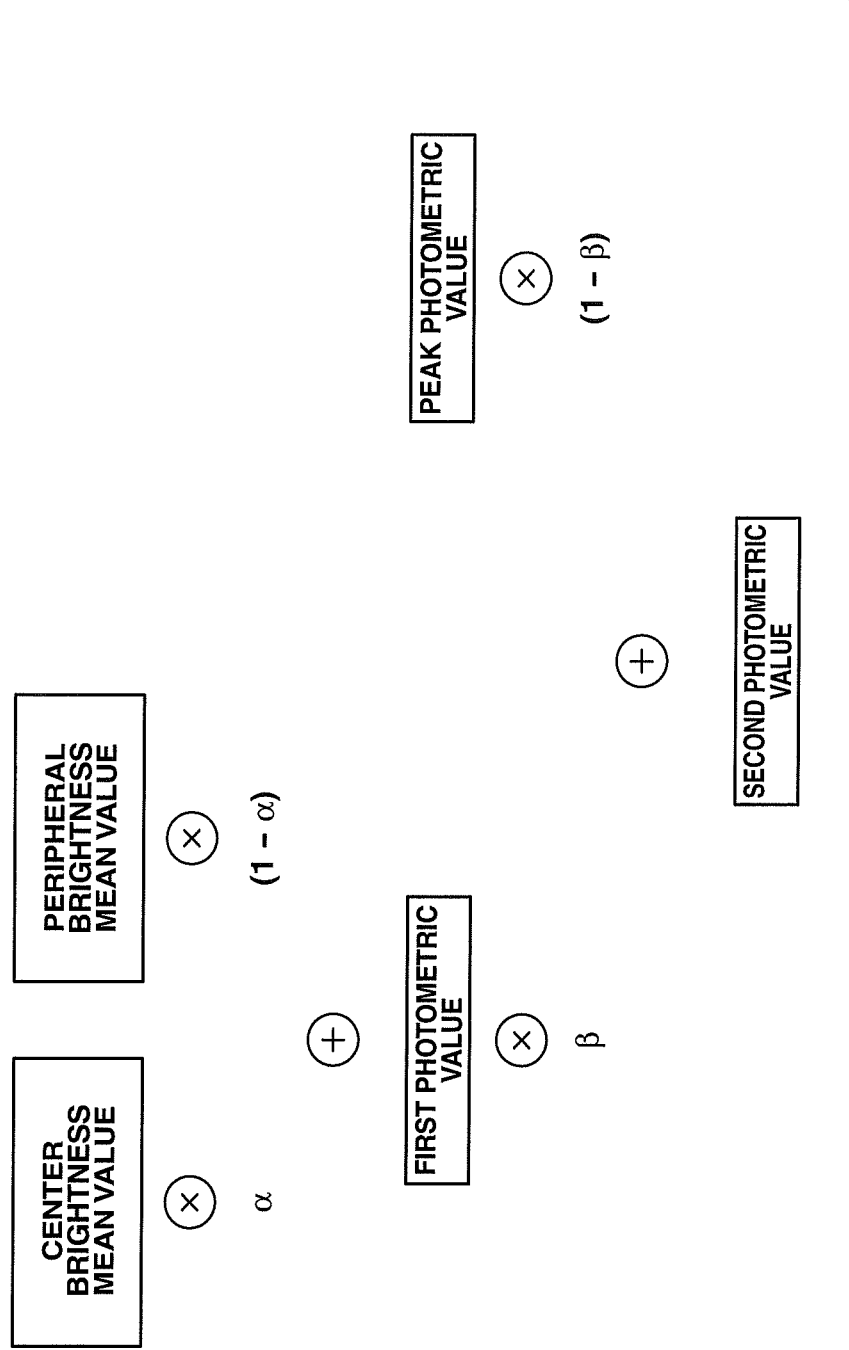
FIG. 9 is an explanatory view for describing processing of the photometry portion of the second embodiment.

As shown in FIG. 9, the endoscope apparatus 8A of the present embodiment adjusts the brightness by means of the second photometric value that is calculated based on the first photometric value that is information regarding brightness that is dependent on the position in the endoscope image 5A and the peak photometric value that is information regarding brightness that is not dependent on the position in the endoscope image 5A.

According to the endoscope apparatus 8A of the present embodiment, in addition to the advantageous effects of the endoscope apparatus 8, since a peak photometric value that is not dependent on position is weighted and added, even in a state in which there are differences with respect to brightness and darkness among regions at the periphery of an image, such as when only one part of the periphery is bright (for example, a region on the bottom right of the screen), it is possible to appropriately adjust the brightness of a region of interest by appropriately determining the brightness of the periphery. It is thus possible to provide an endoscope apparatus with further enhanced operability as well as a control method for the endoscope apparatus.

That is, the operability of the endoscope apparatus 8A is good. Likewise, according to the control method for an endoscope apparatus of the present embodiment, the operability of the endoscope apparatus is good.

The present invention is not limited to the above described embodiments and modifications or the like, and various changes and alterations can be made within a range that does not depart from the spirit and scope of the present invention.

What is claimed is:

1. An endoscope apparatus, comprising:
   a region dividing portion that divides an endoscope image into a center region and a peripheral region;
   a brightness mean value calculation portion that has a peripheral brightness mean value calculation portion that calculates a peripheral brightness mean value that indicates a mean value of a brightness of the peripheral region, and a center brightness mean value calculation portion that calculates a center brightness mean value that indicates a mean value of a brightness of the center region;

a first weighting factor calculation portion that calculates a first weighting factor $\alpha$ (where $0<\alpha<1$) based on a ratio between the center brightness mean value and the peripheral brightness mean value;

a first photometric value calculation portion that calculates a first photometric value based on a sum total of a value obtained by multiplying the center brightness mean value by the first weighting factor $\alpha$ and a value obtained by multiplying the peripheral brightness mean value by $(1-\alpha)$; and a brightness adjustment control portion that generates a brightness adjustment control signal that adjusts a brightness of the endoscope image based on the first photometric value;

wherein when the ratio between the peripheral brightness mean value and the center brightness mean value is in a predetermined range that is centered around a value of 1, even if the ratio changes, the weighting factor calculation portion calculates the first weighting factor $\alpha$ of a same value.

2. The endoscope apparatus according to claim 1, further comprising:

a peak photometric value calculation portion that calculates a peak photometric value based on a peak value of the brightness of the endoscope image; and a second weighting factor calculation portion that calculates a predetermined second weighting factor $\beta$ (where $0<\beta<1$);

wherein the brightness adjustment control portion generates the brightness adjustment control signal based on a sum total of a value obtained by multiplying the first photometric value by the second weighting factor $\beta$ (where $0<\beta<1$) and a value obtained by multiplying the peak photometric value by $(1-\beta)$.

3. The endoscope apparatus according to claim 1, wherein:

the region dividing portion divides the endoscope image into n regions ($n\geq3$);

the brightness mean value calculation portion calculates a brightness mean value for each of the n regions;

the center brightness mean value calculation portion calculates the center brightness mean value based on a brightness mean value of a region positioned at a portion that corresponds to the center region among the n brightness mean values; and the peripheral brightness mean value calculation portion calculates the peripheral brightness mean value based on a brightness mean value of a region positioned at a portion that corresponds to the peripheral region among the n brightness mean values.

4. The endoscope apparatus according to claim 3, further comprising:

a third weighting factor calculation portion that calculates n predetermined third weighting factors $\gamma1$ to $\gamma n$ (where $0<\gamma<1$, and $\Sigma\gamma=1$) that correspond to an order of sizes of the n brightness mean values, wherein the peak photometric value calculation portion calculates the peak photometric value based on a sum total of values obtained by multiplying the respective brightness mean values by the respective third weighting factors $\gamma$ that correspond to the order of sizes of the brightness mean values.

5. A control method for an endoscope apparatus, comprising:

a region dividing step in which a region dividing portion divides an endoscope image into a center region and a peripheral region;

a peripheral brightness mean value calculation step in which a peripheral brightness mean value calculation portion calculates a peripheral brightness mean value that indicates a mean value of a brightness of the peripheral region;

a center brightness mean value calculation step in which a center brightness mean value calculation portion calculates a center brightness mean value that indicates a mean value of a brightness of the center region;

a first weighting factor calculation step in which a weighting factor calculation portion calculates a first weighting factor $\alpha$ (where $0<\alpha<1$) based on a ratio between the center brightness mean value and the peripheral brightness mean value;

a first photometric value calculation step in which a first photometric value calculation portion calculates a first photometric value based on a sum total of a value obtained by multiplying the center brightness mean value by the first weighting factor $\alpha$ and a value obtained by multiplying the peripheral brightness mean value by $(1-\alpha)$; and a brightness adjustment control step in which a brightness adjustment control portion generates a brightness adjustment control signal that adjusts a brightness of the endoscope image based on the first photometric value;

wherein, in the weighting factor calculation step, when the ratio between the peripheral brightness mean value and the center brightness mean value is in a predetermined range that is centered around a value of 1, even if the ratio changes, the weighting factor calculation portion calculates the first weighting factor $\alpha$ of a same value.

6. The control method for an endoscope apparatus according to claim 5, further comprising:

a peak photometric value calculation step in which a peak photometric value calculation portion calculates a peak photometric value based on a peak value of the brightness of the endoscope image, wherein, in the brightness adjustment control step, the brightness adjustment control portion generates the brightness adjustment control signal based on a sum total of a value obtained by multiplying the first photometric value by a predetermined second weighting factor $\beta$ (where $0<\beta<1$) that a second weighting factor calculation portion calculates and a value obtained by multiplying the peak photometric value by $(1-\beta)$.

7. The control method for an endoscope apparatus according to claim 6, wherein:

the region dividing step is a step in which the region dividing portion divides the endoscope image into n regions;

the control method further comprising a brightness mean value calculation step in which the brightness mean value calculation portion calculates a brightness mean value for each of the n regions;

wherein:

in the center brightness mean value calculation step, the center brightness mean value calculation portion calculates the center brightness mean value based on a brightness mean value of a region positioned at a portion that corresponds to the center region among the n brightness mean values; and in the peripheral brightness mean value calculation step, the peripheral brightness mean value calculation portion calculates the peripheral brightness mean value based on a brightness mean value of a region positioned at a portion that corresponds to the peripheral region among the n brightness mean values.

8. The control method for an endoscope apparatus according to claim 7, further comprising:
a third weighting factor calculation step in which a third weighting factor calculation portion calculates n predetermined third weighting factors γ1 to γn (where 0<γ<1, and Σγ=1) that correspond to an order of sizes of the n brightness mean values,
wherein, in the peak photometric value calculation step, the peak photometric value calculation portion calculates the peak photometric value based on a sum total of values obtained by multiplying the respective brightness mean values by the respective third weighting factors γ that correspond to the order of sizes of the brightness mean values.

* * * * *